United States Patent
Natanzon et al.

(10) Patent No.: US 12,406,362 B2
(45) Date of Patent: Sep. 2, 2025

(54) MULTI-MATERIAL DECOMPOSITION FOR SPECTRAL COMPUTED TOMOGRAPHY

(71) Applicant: KONINKLIJKE PHILIPS N.V., Eindhoven (NL)

(72) Inventors: Ludmila Natanzon, Haifa (IL); Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 364 days.

(21) Appl. No.: 18/024,595

(22) PCT Filed: Aug. 26, 2021

(86) PCT No.: PCT/EP2021/073555
§ 371 (c)(1),
(2) Date: Mar. 3, 2023

(87) PCT Pub. No.: WO2022/048976
PCT Pub. Date: Mar. 10, 2022

(65) Prior Publication Data
US 2023/0360201 A1    Nov. 9, 2023

(30) Foreign Application Priority Data
Sep. 4, 2020 (EP) .................................. 20194623

(51) Int. Cl.
*G06T 7/00* (2017.01)
*G06T 11/00* (2006.01)

(52) U.S. Cl.
CPC .......... *G06T 7/0012* (2013.01); *G06T 11/008* (2013.01); *G06T 2207/10081* (2013.01); *G06T 2207/20076* (2013.01); *G06T 2210/41* (2013.01)

(58) Field of Classification Search
CPC ................. G06T 7/0012; G06T 11/008; G06T 2207/10081; G06T 2207/20076; G06T 2210/41; G06T 2211/408; A61B 6/032; A61B 6/482
See application file for complete search history.

(56) References Cited

U.S. PATENT DOCUMENTS

| | | | |
|---|---|---|---|
| 2008/0253504 A1 | 10/2008 | Proksa | |
| 2015/0131883 A1 | 5/2015 | Taguchi | |
| 2021/0312612 A1* | 10/2021 | Modgil | .................. A61B 6/032 |

OTHER PUBLICATIONS

PCT International Search Report, International application No. PCT/EP2021/073555, Nov. 23, 2021.
(Continued)

*Primary Examiner* — Siamak Harandi
(74) *Attorney, Agent, or Firm* — Larry Liberchuk

(57) ABSTRACT

A computer system (MD) and relates method for spectral-data based material decomposition. The system comprises a statistical module (SM) configured to fit, per patch in input spectral imagery, a set of probability distributions (Pk) to a respective vector spectral diagram (5) for the respective patch (A). The patch is one of a plurality of patches in the input spectral imagery obtained by operation of a spectral imaging apparatus. The probability distributions are combinable into a probability map indicative of material type probabilities per image location in the input spectral imagery.

19 Claims, 8 Drawing Sheets

(56) References Cited

OTHER PUBLICATIONS

Xie B. et al., "ROI-Wise Material Decomposition in Spectral Photon-Counting CT", IEEE Transactions on Nuclear Science, IEEE Servi ce Center, New York, NY, US, vol. 67, No. 6, Apr. 1, 2020 (Apr. 1, 2020), pp. 1066-1075, XP011794172.

Long Y. et al., "Multi-Material Decomposition Using Statistical Image Reconstruction for Spectral CT", IEEE Transactions on Medical Imaging, IEEE Service Center, Piscataway, NJ, US, vol. 33, No. 8, Aug. 1, 2014 (Aug. 1, 2014), pp. 1614-1626, XP011554724.

Kim K. et al., "Sparse-View Spectral CT Reconstruction Using Spectral Patch-Based Low-Rank Penalty", IEEE Transactions on Medical Imaging, IEEE Service Center, Piscataway, NJ, US, vol. 34, No. 3, Mar. 1, 2015 (Mar. 1, 2015), pp. 748-760, XP011573922.

Alvarez R. et al., "Energy Selective Reconstructions in X-Ray Computerized Tomography", Physics in Medicine and Biology, vol. 21, pp. 733-744, Sep. 1976.

Liu X. et al., "Quantitative Imaging of Element Composition and Mass Fraction Using Dual-Energy CT: Three-Material Decomposition", Medical Physics, vol. 36, No. 5, pp. 1602-1609, 2009.

Mendonca P.R.S. et al., "A Flexible Method for Multi-Material Decomposition of Dual-Energy CT Images", IEEE Transactions on Medical Imaging, vol. 33, No. 1, pp. 99-116, Jan. 2014.

Liguori C. et al., "Emerging Clinical Applications of Computed Tomography", Medical Devices: Evidence and Research, (Auckl). vol 8, pp. 265-278, 2015.

Kalender W.A. et al., "Evaluation of a Prototype Dual-Energy Computed Tomographic Apparatus I. Phantom Studies", Medical Physics, vol. 13, No. 3, pp. 334339, 1986.

Heismann B.J. et al., "Technology and Image Results of a Spectral CT System", Proceedings of SPIE, vol. 5368, Medical Imaging, Physics of Medical Imaging, May 2004.

Prochowski A. et al., "Material Separation Using Dual-Energy CT: Current and Emerging Applications", RSNA RadioGraphics, vol. 36 Issue 4, pp. 1087-1105, 2016.

Lamb P. et al., "Stratification of Patients with Liver Fibrosis Using Dual-Energy CT", EEE Transactions on Medical Imaging, vol. 34, Issue 3, pp. 807-815, Mar. 2015.

Carmi R. et al., "Material Separation with Dual-Layer CT", Proceedings of IEEE Nuclear Science Symposium Conference Record, 2005, Fajardo, PR, USA, 2005, pp. 1876-1878, 2005.

Goshe L. et al., "An Iodine-Calcium Separation Analysis and Virtually Non-Contrasted Image Generation Obtained with Single Source Dual Energy MDCT", Proceedings of IEEE 2008 NSS-MIC conference in Dresden, Germany, Nov. 2008.

Bazalova M. et al., "Dual-Energy CT-Based Material Extraction for Tissue Segmentation in Monte Carlo Dose Calculations", Physics in Medicine and Biology, vol. 53, No. 9, pp. 2439-2456, 2008.

Carmi R. et al., "Arterial Double-Contrast Dual-Energy MDCT: In-Vivo Rabbit Atherosclerosis with Iodinated Nanoparticles and Gadolinium Agents", Medical Imaging 2010: Biomedical Applications in Molecular, Structural, and Functional Imaging Proc. of SPIE vol. 7626, 2010.

Graser A. et al., "Dual Energy CT: Preliminary Observations and Potential Clinical Applications in the Abdomen", European Radiology, vol. 19, No. 1, pp. 13-23, 2008.

Boroto K. et al., "Thoracic Applications of Dual-Source CT Technology", European Journal of Radiology, vol. 68, pp. 375-384, 2008.

Chae E. J. et al., "Xenon Ventilation CT with a Dual-Energy Technique of Dual-Source CT: Initial Experience", Radiology, vol. 248, Issue 2, pp. 615-624, 2008.

Scheffel H. et al., "Dual-Energy Contrast-Enhanced Computed Tomography for the Detection of Urinary Stone Disease", Investigative Radiology, vol. 42, Issue 12, pp. 823-829, Dec. 2007.

Chen J. et al., "Extended Bayesian Information Criteria for Model Selection with Large Model Spaces", Biometrika, vol. 95, Issue 3, pp. 759-771, Sep. 2008.

Akaike H. et al., "A New Look at the Statistical Model Identification", IEEE Transactions on Automatic Control, vol. AC19, No. 6, pp. 716-723, Dec. 1974.

\* cited by examiner

MULTI-MATERIAL DECOMPOSITION FOR SPECTRAL COMPUTED TOMOGRAPHY

FIELD OF THE INVENTION

The invention relates to a computer system for spectral-data based material decomposition, to an imaging arrangement, to a method of spectral data-based material decomposition, to a computer program element, and to a computer readable medium.

BACKGROUND OF THE INVENTION

Spectral (or multi-energy) X-ray imaging utilizes spectral information as recorded in two or more energy images representing materials density in corresponding two or more energy windows. In a type of spectral imaging, called dual energy imaging, two such energy images are considered. Dual energy imaging may be used in CT (computed tomography) or in radiography.

In spectral imaging, one uses the fact that attenuation values depend on the material imaged and the energy of the X-radiation. The energy images obtained in spectral imaging may be processed into other types of useful spectral imagery, such as monochromatic images, material cancellation images, effective atomic number images, electron density image, and others still.

With recent technical advances, there are several approaches to perform dual energy CT imaging such as dual-source, fast kVp switching, and dual-layer detector configuration. Spectral imaging at more than two energy windows can be done for example by using photon-counting detector equipment.

Another type of spectral imaging includes material decomposition where the energy images are processed into material maps in which contrast is modulated by the amount and concentration of a specific material type. This allows quantitative imaging in relation to the scanned object to learn its material composition.

Spectral imaging may be used for material specific image data segmentation.

R. Alvarez et al in "*Energy selective Reconstructions in X-ray Computerized Tomography*" in Phys. Med. Biol., vol 21, pp 733-744 (1976) had proposed a material decomposition scheme formulated as solutions to a linear system of equations to so achieve decomposition into two different materials accurately.

As an extension, an additional constraint on volume conservation may be used, which allows to resolve the problem of three material decomposition. See for example Liu X, et al in "*Quantitative imaging of element composition and mass fraction using dual-energy CT: three-material decomposition*", in Med Phys, vol 36 (5), pp 1602-1609 (2009).

There are a number of medical applications that call for material decomposition into more than three materials, for example blood, fat, water, air, bone, and contrast agent. For instance, Liver-Fat Quantification (LFQ), requires discrimination between four materials: liver tissue, blood, fat, and contrast agent. Another example of clinical application requiring multi-material decomposition with more than three materials is Virtual Unenhanced Images (VUI), where such materials as bone, soft tissue, fat and contrast are present. VUI has been reported by P. Mendonça et al in "*A Flexible Method for Multi-Material Decomposition of Dual-Energy CT Images*", published "IEEE Transactions on Medical Imaging", vol. 33, No. 1 (2014).

However, for dual energy imaging, such as dual energy CT, decomposition into more than three materials is, in general, an ill-posed deterministic problem. See for example C. Liguori et al in "*Emerging clinical applications of computed tomography*", "*Med Devices (Auckl)*", vol. 8, pp 265-278 (2015).

Many existing material decomposition methods can only discriminate between two, or at most three, materials.

SUMMARY OF THE INVENTION

There may therefore be a need for improvements in spectral imaging.

The object of the present invention is solved by the subject matter of the independent claims where further embodiments are incorporated in the dependent claims. It should be noted that the following described aspect of the invention equally applies to the imaging arrangement, to the method of image-based material decomposition, to the computer program element, and to the computer readable medium.

According to a first aspect of the invention there is provided a computer system for spectral-image-based material decomposition, comprising:

a statistical module configured to fit, per patch in input spectral imagery, a set of probability distributions to a respective vector spectral diagram for the respective patch, the patch being one of a plurality of patches in the input spectral imagery, the input spectral imagery obtained by operation of a spectral imaging apparatus, and the probability distributions combinable into a probability map indicative of material type probabilities per image location in the input spectral imagery. The input spectral imagery is in general multi-dimensional data where each image location is associated with two or more values. The spectral imagery may include two or more energy images.

The spectral imaging apparatus is an X-ray imaging apparatus configured for spectral imaging, such a dual energy imaging apparatus or one with photon counting circuitry, or other.

The patches may be defined by a patch defined in the spectral imagery plane. The patches are a family of (true-) subsets of the spectral imagery in spatial domain. The patches can have any shape or size, and some or all may overlap or may be contiguous. Some overlap among patches allows for more robust fitting. The family of patches may not cover the whole of image plane. The patch definer may use kernel functions to define the patches.

The number of probability distributions model per spectral diagram is indicative of the number of different material types for the said patch. Advantageously, and in embodiments, this number may be four or more allowing material decomposition into at least four materials, which is useful for medical applications.

In embodiments, the system comprises a combiner configured to combine the probability distributions into a probability map indicative of material type probabilities per image location in the input spectral imagery.

In embodiments, the combiner is configured to perform a combination operation to combine, per image location in the image, the set of probability distributions fitted to spectral diagrams for those patches that include the respective image location, to so obtain the probability map. A single such model may be used per patch to define a partial probability map. A global probability map may be obtained by using plural partial models that contain the respective image location. The spectral diagram of all patches that include the respective image location may be used. The combination operation may be understood as ensemble averaging where partial models are combined into one global model.

In preferred embodiments, the combination operation by the combiner includes adapting one or more contributions of the probability distributions to the probability map, based on their likelihood values per image location. Specifically, in embodiments, the combination operation includes averaging the probability distributions per image location. A weighted averaging may be used, with at least relative down-weighting. The probability distributions with low likelihoods may be down-weighted and/or those with higher likelihood may be given higher weights. Instead of such a soft-adaptation-scheme, a hard-adaptation-scheme may be used with thresholding, wherein contributions below a threshold are ignored. Adapting the one or more contributions by reducing, or eliminating, relatively low likelihood contributions allows for a more robust fitting. The adaptive combination operation favors patches with "good statistics" with enough samples when computing the probability map.

In embodiments, the system comprises a classifier configure to classify the probability distributions according to material type.

In embodiments, the statistical module configured to fit the probability distributions based on a maximum likelihood algorithm.

In embodiments, the said maximum likelihood algorithm includes the expectation-maximization [EM] algorithm.

In embodiments the number of probability distributions per spectral diagram is established based on a metric. The may be any one of i) Bayesian model selection metric and ii) an information theoretic model selection metric.

Alternatively, the said number is pre-set or pre-defined. Then number may be supplied by a user though a user interface. The number may be in the range from [3,4,5] or other.

In embodiments, the set of probability distributions may represent a mixture model.

In embodiments, the probability distributions are Gaussians.

Mix model comprises a weighted sum of different probability distributions. The set of probability distribution may be parameterized. The fitting operation may include adjusting parameters based on information in the respective spectral diagram.

In another aspect there is provided an imaging arrangement comprising an X-ray dual energy imaging apparatus, and the system as per any one of the previous claims.

In another aspect there is provided a computer-implemented method of spectral-data based material decomposition, comprising: fitting per patch in input spectral imagery, a set of probability distributions to a respective vector spectral diagram for the respective patch, the patch being one of a plurality of patches in the input spectral imagery obtained by operation of a spectral imaging apparatus, the probability distributions combinable into a probability map indicative of material type probabilities per image location in the input spectral imagery. The method may further comprise combining the probability distributions into the probability map indicative of material type probabilities per image location in the input spectral imagery.

In embodiments, the method comprises defining patches in the spectral imagery.

In embodiments, the method comprises forming the spectral diagrams.

In embodiments, the method comprises combining, per image location in the image, the set of probability distributions fitted to spectral diagrams for those patches that include the respective image location, to so obtain the probability map.

The proposed system and method apply statistical mixture models, such as of the Gaussian type (GMM), to spectral diagrams in spectral domain for spatially defined subsets (referred to herein as patches) of the original spectral imagery.

Each pixel/voxel in spatial domain of the spectral imagery has two or more characteristics, where each of these characteristics is a measurement of the density of the matter in this pixel/voxel made in the respective energy window. In case of dual-energy imaging, the measurements are performed in low and high energy windows, and each spatial pixel is represented by two-coordinates pixel in the two-dimensional spectral domain. In case of dual-energy imaging, those measurements in low and high energy windows allow to compute photo-electric attenuation and scatter components of the X-ray interaction with the scanned tissues, which, in turn, provides additional information for multiple clinical applications. In general, multiple-energy measurements in n different energy windows define a transform S' from the spatial domain of the scanned volume to the n-dimensional spectral domain. The image of the S' in the spectral domain will represent the density of the pixels as a function of the measurements values combinations, or, in the discrete case, the histogram with respect to the measurements values combinations.

The proposed system uses a statistical approach to solve a clustering problem of points in the spectral domain, where each cluster can be attributed to one individual material type. Based on this clustering one can then define the probabilities of the pixels/voxels of the original image to represent a certain material. Specifically, the resulting local or partial models can be used to compute partial material type probabilities maps. By averaging the resulting partial probabilities for pixels of the original image, a global probability map can be computed. This per patch approach fosters better robustness and management of the ill-posedness of multi-material decomposition into, in particular, more than three materials. Instead of processing the whole image at once, the proposed partial per-patch approach fosters better convergence of the partial models, each being defined by the respective set of probability distributions such as Gaussian. Gaussian Mixture models produced have been found to yield good results. The resulting fitted probability distributions have been found to be better localized than in global approaches, with Gaussian having smaller spread. More concentrated Gaussian in turn allow for a more accurate material type classification. Probability distributions other than Gaussian may be used instead or in addition.

In another aspect there is provided a computer program element, which, when being executed by at least one processing unit, is adapted to cause the processing unit to perform the method as per any one of the above-mentioned embodiments.

In another aspect still, there is provided a computer readable medium having stored thereon the program element.

Definitions

"user" relates to a person, such as medical personnel or other, operating the imaging apparatus or overseeing the imaging procedure. In other words, the user is in general not the patient.

"object" is used herein in the general sense to include animate "objects" such as a human or animal patients/subjects, or anatomic parts thereof but may also include inanimate objects such as an item of baggage in security checks or a product in non-destructive material testing or compositional analysis. However, the proposed system will be discussed herein with main reference to the medical field, so we will be referring to the "object" as "the patient/subject" or a part of the patient, such as an anatomy or organ, or group of anatomies or organs of the patient.

"Material decomposition" are image-based techniques to learn material composition of an imaged object. "Material" as used herein includes elemental materials or compounds, or mixtures of such materials Material decomposition is based on spectral imagery, which is multi-dimensional comprising more than one value per pixel/voxel of the scanned volume, as an opposed to non-spectral imagery which comprises only one value per pixel/voxel.

BRIEF DESCRIPTION OF THE DRAWINGS

Exemplary embodiments of the invention will now be described with reference to the following drawings, which, unless stated otherwise, are not to scale, wherein.

DETAILED DESCRIPTION OF EMBODIMENTS

Figure 1:
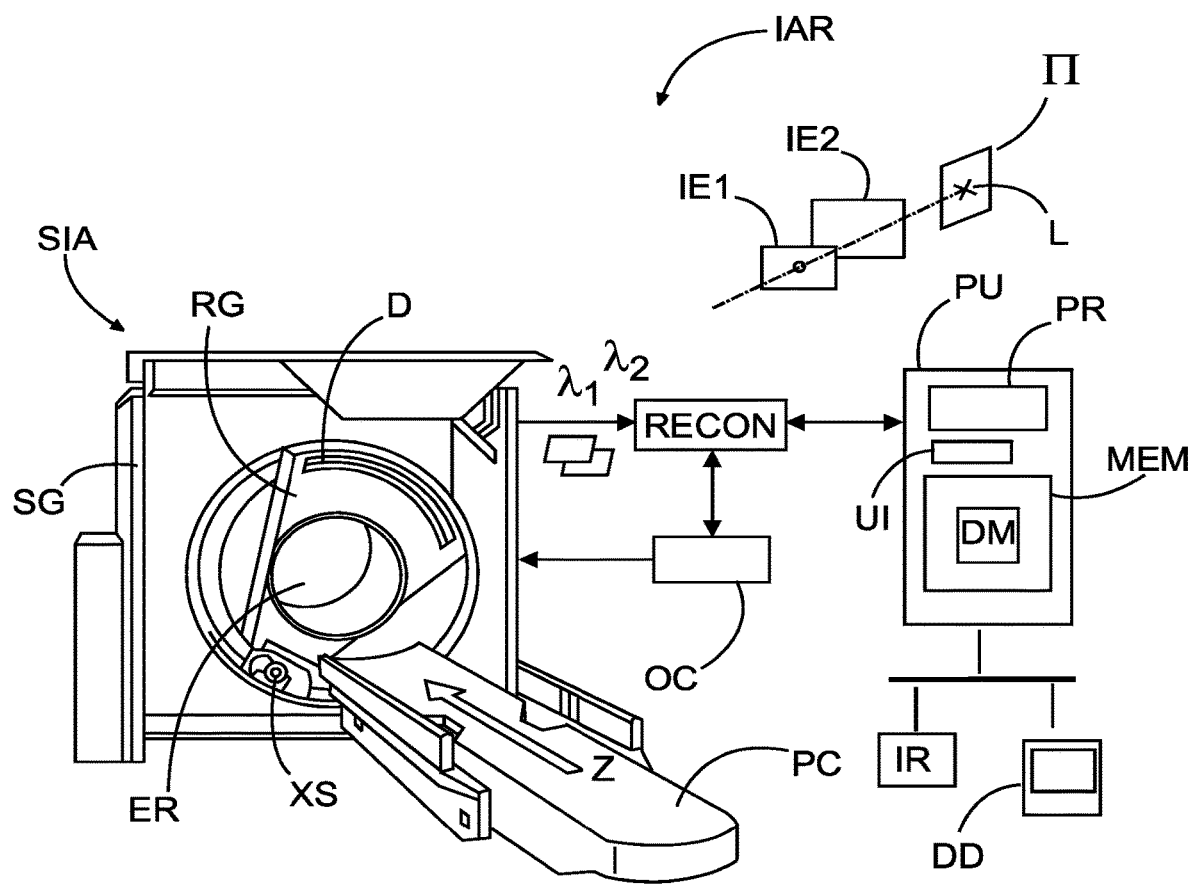
FIG. 1 shows a schematic block diagram of a spectral imaging arrangement.

FIG. 1 schematically illustrates an example imaging arrangement IAR, including an X-ray imaging apparatus SIA and an image processing system MD. The imaging apparatus may be a CT scanner SIA. The scanner SIA includes a stationary gantry SG and a rotating gantry RG. The rotating gantry is rotatably supported by the stationary gantry SG and rotates around an examination region ER and a portion of an object or subject therein about a Z-axis. A radiation source XS, such as an X-ray tube, is supported by and rotates with the rotating gantry RG around the examination region ER. The radiation source XS emits in general wideband polychromatic X-ray radiation that is collimated to form a generally fan, wedge, or cone shaped X-ray radiation beam that traverses the examination region ER.

A radiation sensitive detector array of detector D may subtend an angular arc opposite the radiation source XS across the examination region ER. The detector array includes one or more rows of detector pixels that are arranged with respect to each other along the Z-axis and detects X-ray radiation traversing the examination region ER. The detector provides projection (raw) data.

A reconstruction system RECON, referred to herein as the reconstructor, reconstructs the projection data, generating spectral image data. As will be explored in more detail below, the system MD processes the spectral image data to obtain processed spectral image data.

A subject support PC, such as a couch, supports a subject or object (e.g., a phantom) in the examination region ER. The subject support PC is movable in coordination with performing an imaging procedure so move the subject or object with respect to the examination region ER for loading, scanning, and/or unloading the subject or object.

An operator console OC may include a human readable output device such as a display monitor DD, etc. and a user input device such as a keyboard, mouse, etc. The console OC further includes a processor (e.g., a central processing unit (CPU), a microprocessor, etc.) and computer readable storage medium (which excludes transitory medium) such as physical memory. The operator console OC allows user to control the imaging procedure.

The arrangement IAR may further include a processing unit PU such as workstation to image-process raw projection data acquired by the imager. The operator console OC and workstation may be arranged in the same computing system. The reconstructor RECON may run on the workstation PU.

Whilst the principles disclosed herein are described with main reference to CT or other volumetric/rotational imaging modalities such as C-arm imagers or similar, they are of equal application to projection imaging in radiography.

In more detail, during imaging operation, the patient, or at least a region of interest ("ROI") of patient, resides in the examination region ER. For example, the patient may lie on the patient couch PC arranged at least partly inside the donut shaped CT examination region ER.

The X-ray source XS is energized. X-radiation emerges from the source XS, traverses the examination region ER and the ROI/patient, and is then registered at the far end at the X-ray sensitive pixels that make up an X-ray sensitive surface of the X-ray detector D.

The impinging X-radiation causes the X-ray sensitive pixels to respond with electrical signals. The electrical signals are processed by data acquisition circuitry of the scanner IA to produce digital projection raw data. The projection data in projection domain may be processed by the re-constructer RECON to compute, for example, cross sectional imagery of the ROI in image domain. The reconstructed imagery may be further processed as indeed envisaged herein into spectral imagery. The spectral imagery and/or the reconstructed imagery may be stored or displayed on a display device DD etc. The reconstructed/spectral imagery may be examined by a user for therapy or diagnostic purposes.

The re-constructer RECON is a transformer that transforms from projection domain located at the detector surface into image domain which is located in the examination region. The reconstructor RECON may implement any one or more of different types of reconstruction algorithms, such as Radon transform based algorithms, in particular filtered back-projection (FBP). Fourier-transform type algorithms are also envisaged, and so are iterative, algebraic or machine learning based reconstruction algorithms.

The reconstructed cross-sectional imagery can be thought of as image values that are assigned by the re-constructer to grid points, referred to as voxels, in the 3D portion that makes up the examination region. There may be a plurality of such sectional images in different section planes of the image domain. The plurality of section images in different such planes form a 3D image volume. Location for image values in a given cross sectional image may also be referred to herein as (image) pixels. The As briefly mentioned, the imaging apparatus SIA, such as the CT scanner in FIG. 1, is configured for spectral imaging. The X-ray imaging apparatus SIA thus produces sets of spectral projection raw data $\lambda_{j, j \geq 2}$ two or more energy windows. The re-constructer RECON produces therefrom respective spectral sectional imagery $I_{Ei}$.

Reconstructed spectral imagery (and the spectral projection raw data) is multi-dimensional data. This is illustrated in the upper portion in FIG. 1. In spectral imaging, for each image location L in any given image plane Π, there are associated not only one but plural image values $E_j$, at least one such value for each energy window. For example, in dual imaging, a special instant of spectral imaging, there are two such image values $E_1$, $E_2$. The X-radiation emitted by the source XS is not generally monochromatic but is polychromatic. In other words, the X-ray photons that make up the X-radiation have energies in a range of values, an energy spectrum, rather than a single energy. Each such value $E_j$ for a given image location L represents contrast for different such energies or energy ranges. In spectral imaging, it is this spectral information that is harnessed. Intensities detected at the detector D depend on material and energy window, and this differentiation is carried over into image domain for the reconstructed sectional imagery. Each set j of spectral projection raw data $\lambda_{j, j \geq 2}$ for each energy window $E_j$ is hence reconstructed by reconstructor RECON into a respective "energy image" $I_{Ej}$, thus resulting in plural image values $E_j$ for any given image location L as mentioned above.

In this manner, spectral imaging allows resolving image contrast into plural energy windows. Resolving into two such energy windows, high E2 and low E1, is sufficient for present purposes and is usually referred to as dual energy imaging. The low energy (about <30 keV) image $I_{E1}$ represents attenuation mainly by photoelectric absorption, whilst the higher energy image $I_{E2}$, (E2>30 keV) represents attenuation mainly by Compton scattering. Each energy image $I_{E1}$, $I_{E2}$ captures different aspects of attenuation.

However, resolving in more than two such energy windows, as into three, four or more such energy windows is also envisaged in spectral imaging. In embodiments, resolving into two or more than two energy values may be obtained at the detector-side by having a specially configured detector D that is equipped with counting circuitry (not shown). The counting circuitry classifies incoming intensities in projection domain into different energy bins against a set of energy thresholds. Other detector-side solutions include dual or multi-layer detector configurations. Source-side solution are also envisaged, such as dual- or multi-source imagers, or those with a single source XS equipped with fast kVp switching circuitry.

Although we will mainly refer below to dual imaging with two energy windows, E1,E2, with two energy images $I_{E1}$, $I_{E2}$, this is not to be construed as limiting. Specifically, principles of the present disclosure are applicable to all form of spectral imaging with more than two energy windows $E_{j, j>2}$ and thus more than two energy images (for example, photon-counting based imaging) $I_{Ej, j>2}$ are specifically envisaged herein in embodiments.

Spectral imaging is useful for diagnostic purposes in particular as it allows extracting more information as traditional energy integrating imaging would allow, where the spectral information described above is usually lost. In traditional imaging, the energy is integrated and is the total energy deposited that confers image contrast. The different energy images may be of interest in themselves, but the spectral imagery may be processed into other imagery still, such as a virtual monochromatic image, a contrast agent quantitative map, a virtual non-contrast image, an electron density image, and/or other spectral imagery.

Of particular interest herein is a yet further type of spectral imagery, which is referred to as material maps in material decomposition imaging. This type of imaging allows resolving image contrast into different material types. For instance, one can produce a fat image, water image and bone image and so forth, where each contrast represents the amount or concentration of each respective material fat, water, bone at a given image location L.

Applications of material decomposition imagery abound, for instance, medical image segmentation, bladder or kidney stone detection, liver-fat quantization (LFQ), and many others still.

The imaging arrangement IAR as proposed herein includes a computerized system MD configured for material decomposition, also referred to herein as the "material decompositioner MD" or simply the "decompositioner MD".

The decompositioner MD may be implemented by one or more computing systems PU. It may be arranged centrally or on one or more servers in a distributed or cloud service architecture communicatively coupled to one or more imagers through a wired or wireless connection. Alternatively, the MD is implemented in a single computing system, such as a workstation, associated with a single imager SIA.

The spectral imagery supplied by the imager SIA may be first stored in an image storage, such as a PACS (picture archiving and communication system) in a hospital information system (HIS), and is then retrieved therefrom and processed by the decompositioner MD. Alternatively, the spectral imagery may be forwarded direct via wired or wireless communication from the imager IA or its workstation to the decompositioner MD.

The decompositioner MD may be arranged as one or more software modules that run on a single computing systems PU or, in a distributed architecture, on more than one computing systems PU, such as servers etc. A server-side arrangement MD may be useful as a group of imagers SIA in a geographical area may be supported, such as, for example, imagers SIA from different medical facilities.

The one or more computing systems PU include one or more processers, for instance capable of high-speed processing such as those of multi-core design. Parallel computing may be used. The computing system PU further includes one or more memories MEM where instructions are stored to implement the material decompositioner MD. Instead of, or in addition to, software-based implementations, at least a part of the material decompositioner MD may be arranged in hardware, for example hard-coded into dedicated circuitry, such as ASICS or others, preferably integrated into the imager SIA or its workstation.

Figure 2:
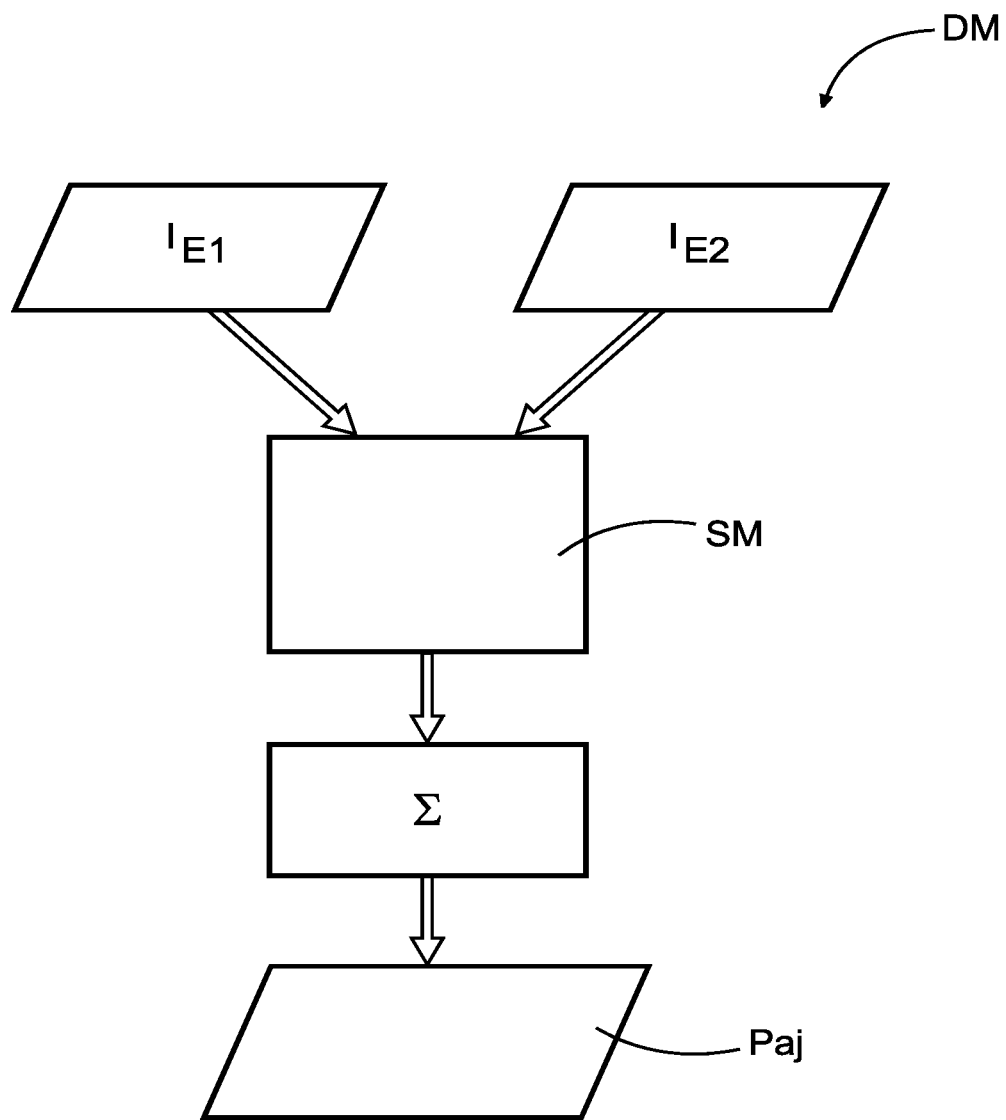
FIG. 2 shows a block diagram of a dual-energy based material decomposition system.

Reference is now made to FIG. 2 which shows a schematic block diagram of the decompositioner DM including components thereof.

Input spectral imagery, including at least two different energy images, such as the high and low energy images $I_{E1}$ and $I_{E2}$ in dual imaging, are received at a statistical module SM.

As explained above, the input spectral imagery relates to spatial domain where each pixel/voxel represents a location (x,y,z) in the examination region ER, with respective attenuation values for different energy windows E1,E2 associated therewith. The statistical module SM as envisaged herein processes data related to the input imagery to identify plural materials present in the ROI. It is envisaged herein that the material decomposition can be done robustly for two, three, but more specifically, for four or more materials.

In more detail, the statistical model SM attempts to identify the materials based on fitting a set of probability distributions, not to the input spectral imagery themselves, but in a spectral space associated with the input spectral imagery. This spectral space, as opposed to the spatial domain in which the input spectral imagery is located, can be represented by a spectral diagram, or more specifically, by a vector spectral diagram, with dimension corresponding to the number of energy windows. For example, in dual energy imaging envisaged herein in embodiments, there are two dimensions with two axes in this spectral space indicating the respective attenuation responses in the energy windows, high and low. In photon counting applications for more than two energy windows, the spectral diagram has dimension three or higher, with three or more axes accordingly. The spectral diagram has a histogram structure, where for each point with energy coordinates $(e_1, e_2, \ldots e_j)$, there is associated the total sum of attenuation responses as per the spectral images, preferably normalized. For example, in dual imaging, the spectral diagram is thus a surface in 3D space $(e_1, e_2) \rightarrow n$, with n the normalized count over all those image locations with responses at energy combination $(e_1, e_2)$.

The input energy images $I_{E1}$, $I_{E2}$ are hence first transformed into such a vector spectral diagram in spectral domain, and the statistical module SM operates on the said vector spectral diagram, referred in the following as the "spectral diagram". The spectral diagram may be smoothed to facilitate the fitting operation by statistical module SM, so as to reduce the stepped appearance of the spectral diagram.

Rather than attempting to fit the probability distributions to the whole spectral diagram at once, a localized/partialized approached is envisaged herein instead as will be detailed below. The input spectral imagery is sub-divided in spatial domain into patches, sub-sets of the input spectral images. A respective spectral diagram is then prepared for each of the patches separately and the statistical module SN then fits the probability distributions per patch. A plurality of probability distributions so fitted form a respective local/partial statistical model. Because the fitting is done per patch, a set of partial models is obtained this way, one such partial model per patch. Each partial statistical model may be rendered as a partial probability map per patch.

An optional combiner $\Sigma$ combines the partial models for some or all patches to obtain a global probability map $Pa_j$ for the whole image plane. In the probability map, partial or global, each entry at a given image location L represents the probability for each of the three or more materials found. The probability map may be displayed on a display device DD color- or grey-value coded.

It will be understood that the proposed method can be applied for dual or triple material decompositions, although the full benefits of the proposed scheme are most palpable in material decomposition tasks for more than three materials, such as four, five, six or even more still. Specifically, double-digit material decomposition can be done with the proposed system MD in a robust manner.

The decompositioner MD may include a use interface UI, such as a graphical user interface GUI, for the user to select the number of materials for the material decomposition to be computed. The graphical user interface (GUI) may include one or more check boxes, a dropdown menu for example. A GUI is not requirement herein, as textual input via textboxes in response to keyboard input is also envisaged herein, and so are other user interfaces UI.

Figure 3:
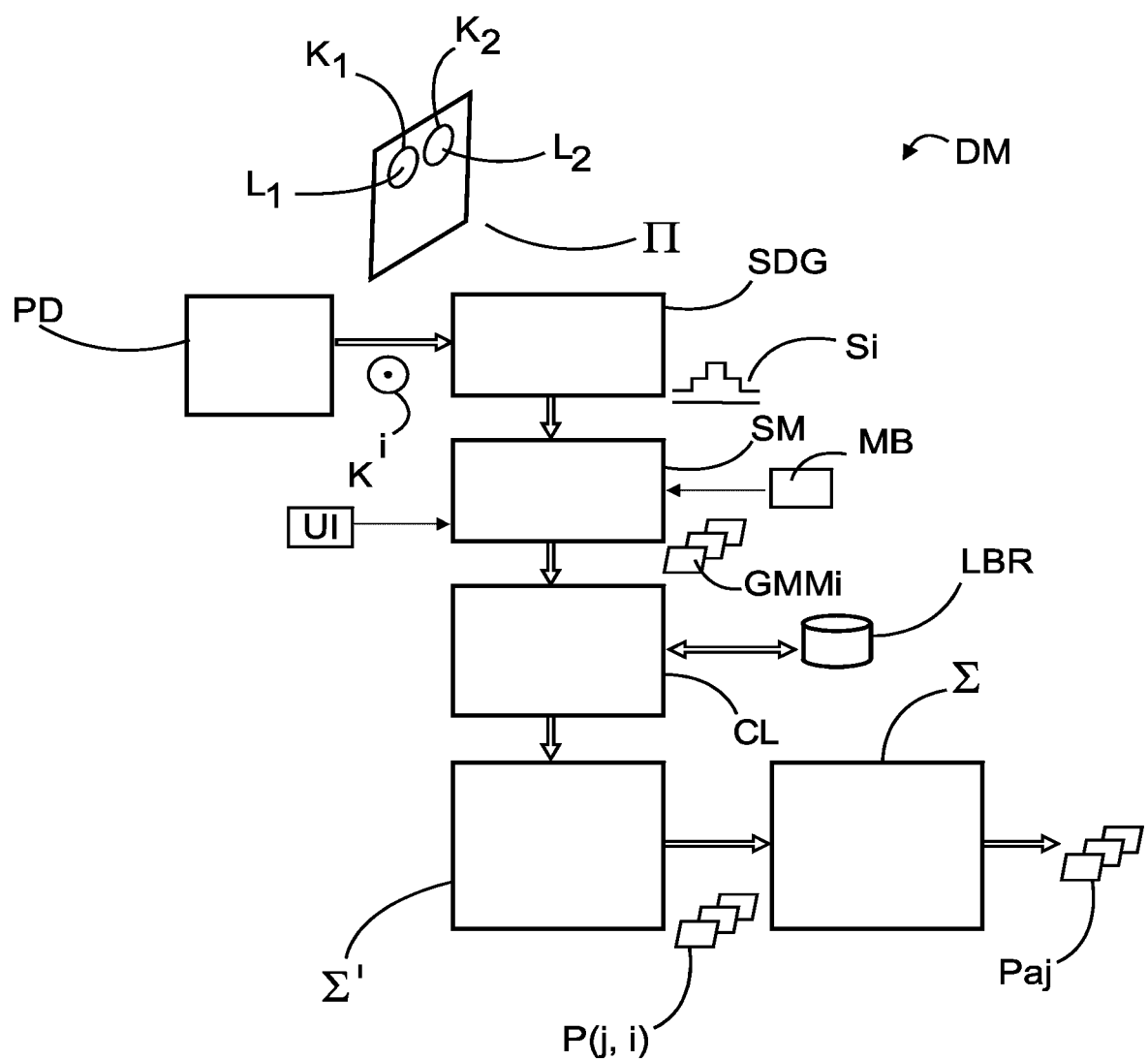
FIG. 3 shows further components of the material decomposition system.

Reference is now made to FIG. 3, which shows a block diagram to provide more details of the material decompositioner DM.

A patch definer PD uses one or more kernels of any shape and size to slide in a step width over image plane $\Pi$ in spatial domain to define patches K1, K2 at image locations L1, L2, respectively, for spectral imagery $I_{E1}$, $I_{E2}$. The patches K1,2 can be of any shape and/or size and may be contiguous or may be overlapping as shown in FIG. 3 schematically. The whole image plane may be tiled with such patches K1,2, but this may not necessarily be so in embodiments where only a certain image region is analyzed. For exemplary purposes, only two patches K1,K2 at two locations L1,L2 are shown in FIG. 3, but this is for illustration only, it being understood that there are usually more than two patches depending on the size of the input imagery. The size and/or the shape of the patches can be adjusted to the data for better quality of the statistical results. On the one hand, a given patch preferably includes enough pixels to provide for better convergence of the implemented algorithm. On the other hand, it may be preferable to restrict patch size so as not to include more than the envisaged number of different types of issues and/or materials. Preferably, the size of a patch should be in the order of a few hundred pixels/voxels. In case computational resources are only of minor concern, one may use different exploratory runs of the proposed algorithm on patches of different sizes and/or shapes, and then filter out all those patches that result in partial models with only low likelihood. Another design/hyper-parameter for the proposed algorithm, apart from patch size or shape, is the amount of overlap among the patches. This amount may be quantified in terms of percentage of overlap between neighboring patches. For more robustness, a higher amount of overlapping is desirable. The design parameter for overlapping may be constant or may be adaptive. A smaller step width, and hence a higher amount of overlap, may be used for regions with strongly varying values, whilst a larger step width, and hence lower amount of overlap, may be used for more homogenous image regions.

Each such image patch $K_i$ defined by definer PD is transformed by spectral diagram generator SDG into a respective spectral diagram $S_i$. For dual imaging, the respective local diagram $S_i$ per patch has two dimensions, one for each energy window E1,E2. Each point (e1,e2) in the spectral diagram $S_i$ in spectral space (in this case a plane) may thus represent the frequency f=n/N of measurements in the two energy images IE1,IE2 as seen at one or more spatial locations n over all locations N.

The order of operation of patch definer PD and spectral diagram generator SDG may be reversed. The whole or a part of the spectral image is transformed first into a global spectral diagram, which is then divided into a set of (partial) spectral diagrams $S_i$. The patches in spatial domain may then be defined as the inverse image of each partial diagram $S_i$ in spatial domain. Each partial diagram $S_i$ hence gives rise to a respective patch in spatial domain, each such patch $K_i$ comprising locations whose measurement at the respective locations fall into the respective partial diagram $S_i$. Each spectral diagram Si is hence associable with a patch $K_i$ in spatial domain.

The patches $K_i$ may or may not be topologically connected.

For each spectral diagram $S_i$, statistical module SM builds a respective partial model by fitting parameters of a family of probability distributions to data as recorded in the respective said spectral diagram $S_i$. A model builder MB may define a number of hyper-parameters to inform the statistical fitting operation by the statistical module SM. In embodiments, statistical mixture models are used. Such mixture models are represented by a weighted sum of individual parameterized probability densities or distributions. In embodiments, Gaussian partial mixture models $GMM_i$ are used as adapted to the respective spectral diagram $S_i$ per patch. Each probability density in the mixture model per patch Ki has its own parameters that are adapted by the statistical module, such as the respective mean and variance/ standard deviation.

In particular, the number of probabilities distributions to be used for each spectral diagram $S_i$ per patch is such a hyper-parameter and this number may be defined by model builder MB in embodiments. The number of probability distributions for each partial mixture model $GMM_i$ may correspond to the number of materials one expects to find. This number may be predefined by user through user input UI or may be computed based on the spectral data by model builder MB. This number may be the same for each patch, or may vary and can be computed by model builder MB based on certain metrics as will be described in more detail above. The number of probability distributions in each partial model $GMM_i$ may be said to form a "group" or "mixture". Whilst we refer herein to each partial mixture model as $GMM_i$, it is understood that this partial model may not necessarily be Gaussian. Other types of probability distributions may be used instead. Also, parameterized models are not a necessity herein, and non-parametric statistical methods are also envisaged herein.

In embodiments, the statistical module SM operates to fit a linear combination of the respective group of probability distributions to the respective spectral diagram to obtain the respective partial statistical model $GMM_i$ for the given patch Ki/spectral diagram Si. The fitting operation may be done according to a statistical algorithm such as a maximum likelihood algorithm. In embodiments, to be described in more detail below, the expectation maximization algorithm is used, but other maximum likelihood or non-maximum likelihood methods are equally envisaged herein. Again, whilst Gaussian mixture models have been found to work particularly well, the present principles are not confined to Gaussian mixture modeling and other types of statistical probability distributions may be used instead. Equally, statistical mixture models, whilst beneficial herein are not necessarily the only model types that may be used herein. Non-mixture type statistical modelling approaches may be considered herein in the alternative.

The output of the statistical module SM is a respective "partial" or partial model $GMM_i$ for each patch $K_i$/spectral diagram $S_i$. Because each patch $K_i$ is associated with its respective spectral diagram $S_i$, "$K_i \leftrightarrow S_i$", an operation on or a statement in relation to the respective (local) diagram $S_i$ may hence therefore be referred to herein as such an operation or statement per patch $K_i$.

Operation of the statistical module may be understood as a clusterer that clusters each spectral diagram according to the number of probability distributions for the materials. However, at this stage it may still not be known which probability distribution so found represents which material. The classification of each probability distribution per patch and partial model $GMM_i$ into a spectral material type is done by a classifier CL. Each probability distribution is preferably parameterized. Parameters may include mean u and variance $\sigma^2$ such as is the case for Gaussian or exponential families more generally. It is these parameters that may be adjusted by the statistical module SM, based on the data in each spectral diagram per patch. The parameters describe shape and location of the respective probability distribution in the spectral diagram and hence so define the clusters. The parameters have been found to be a tell-tale of the material type. As will be explained more fully below, the classifier CL uses in embodiments a library LBR of previously stored probability distribution prototypes which are already assigned to a respective material type. The classifier CL then compares the probability distributions for similarity with the prototypes in the library to establish the material type. The parameters of the fitted and prototypical distributions may be used to determine similarity. Alternatively or instead, machine learning may be used for this classification task. The classifier CL, preferred as it is, is optional as in some cases it may only be the number of materials for each patch that are of interest for a "coarse" material decomposition analysis.

A partial model combiner $\Sigma'$ may be used to combine the partial models GMMI for a given spatial image location in the original image plane Π. It will be appreciated that in general each image location L is covered by more than one patch such is the case for overlapping patches. Specifically, each image location is thus associated not only with one, but with a plurality of such patches that cover the said location, and hence with the same plurality of spectral diagrams and, consequently, with the same plurality of respectively fitted partial models $GMM_i$. In yet other words, each image location is thus associated with the said plurality of partial models GMMI.

It is the said plurality of partial models GMMI associated with a given image location L that are combined by the partial combiner $\Sigma'$. This partial combination operation per image location yields partial probability maps $P_{i,j}$ which may be of interest in themselves if only a local material decomposition analysis is sought. However, for a global analysis, a global probability map may be required. The global probability map is obtained by global combiner $\Sigma$ in a further combination operation. The global combiner $\Sigma$ may ensemble-average the partial probability maps $P_{i,j}$ to produce a global probability map $Pa_j$ as output. As will be explored in more detail below, a thresholding scheme, hard or soft, may be used in the combination operations by combiners $\Sigma''$, $\Sigma$, to down-weigh, or remove, models with low likelihood contributions.

Any one, or any sub-combination of two or more, or all of the above described components of de-compositioner MD may be integrated into a single computational/functional component. Alternatively, the decompositoner MD is implemented in distributed fashion across more than one such computational/functional components.

Operation of the above described components will now be described in more detail, using Gaussian mixture models (GMM) as an example, with the understanding that the present disclosure is applicable to any type of probability distribution with density in the exponential family, or to those with other densities.

Turning first in more detail to operation of the patch definer PD, this may be implemented by using a parametrized family of relatively small kernels of square or round shape which cover parts or the whole of the image plane, with or without overlaps. Having some or all kernels overlap is advantageous. The more overlap is applied, the more information is available for each pixel of the original image, which in turn helps secure better quality of the resulting probability map.

The family of the kernels is characterized by the size of the kernel, its shape (such as square/rectangle, curved such as circle shaped or elliptic shapes), and the step width, that is, the amount by which the kernel is shifted from a current to the next position in the image plane. It is not necessarily herein for kernel shape and/or size to remain constant as either one or both of shape and size may vary with position.

For each kernel position, a respective local spectral diagram is built by binning according to the energy density as recorded in the two (or more) energy input images IE1, IE2 for all pixel positions covered by the current kernel position.

Operation of the classifier CL based on the library of pre-classified probability distribution prototypes will now be explained in more detail.

Classification, or labelling, of the Gaussians in the respective partial models $GMM_i$ may be done by comparing the fitted Gaussians to a set of labelled pre-computed prototype Gaussians held in in library LBR, a Ground Truth Gaussians Library (GTGL), and finding one or more closet matching prototype Gaussians. This library of labelled Gaussians plays the role of the Ground Truth in the proposed algorithm. The label represents the material type (eg, fat, water, Iodine, etc) to which the respective Gaussian prototype is attributed.

The library LBR stores the set of parameters for each prototype-Gaussian, which fully defines the prototype and hence the respective material label. For example, for bivariate prototype Gaussians the set of parameters stored in the GTGL may be written as $(\mu_X, \mu_Y, \Sigma_{XX}, \Sigma_{XY}, \Sigma_{YX}, \Sigma_{YY}$, where $\mu_X, \mu_Y$ are the coordinates of the mean in the spectral plane where the respective Gaussian is centered, and $\Sigma_{XX}, \Sigma_{XY}, \Sigma_{YX}, \Sigma_{YY}$ are the parameters of the covariance matrix that define the spread of that prototype.

The library LBR may be built up manually or in an automated fashion.

In manual labeling, the Gaussians resulting from the partial models $GMM_i$ for the respective image patches are used. Historic imagery may be used as found in PACS (picture archiving and communication system) or other image repositories. The labelling may be done by a human expert. In a good number of cases, the material label will be known a priori, such as from the nature of the historic examination. Meta-data and patient records as held alongside the imagery in the PACS etc may be used to aid labelling.

In automatic ROI labeling, a segmentation algorithm is used to segment the spatial energy images $I_{E1}, I_{E2}$ in spatial domain into known materials regions. The partial models $GMM_i$, are then computed as described above for the corresponding spectral diagram in the spectral domain. The resulting Gaussians are then labelled accordingly and entered into the library GTGL as new prototypes. A semi-automatic version is also envisaged, where the segmentation in spatial domain is done manually.

The classification operation as administered by the classifier CL can be hard or soft. In hard classification, the single best matching prototype is found in the library LBR based on a suitable nearest neighbor measure. Interpolation in a look-up structure such as LUT may be used to interpolate over the parameters. In soft classification, the nearest neighbor match is evaluated against a threshold which may result in plural "nearest neighbor"—prototypes as candidates for the correct material label. In this soft classification embodiment, there is no single best matching probability distribution. In this case, the result is not a single material type assignment, but a set of material types with associated probabilities, each computed from the nearest neighbor candidate probability distribution from the library. The material type labels in the set are those with which the nearest neighbor candidate probability distributions from the library LBR have been labeled with.

The one or more nearest neighbors may be found by a suitable measure such as squared Euclidean distance, cross-entropy or, more generally, the Kullback-Leibler divergence:—

$$D_{KL}(p,q) = \ln\left(\frac{\sum_2}{\sum_1}\right) + \frac{\sum_1^2 + (\mu_1 - \mu_2)^2}{2*\sum_2^2} - \frac{1}{2} \quad (1)$$

wherein $\{\mu_1, \Sigma_1\}$ and $\{\mu_2, \Sigma_2\}$ are parameters defining the Gaussians.

As an alternative, machine leaning may be used for the classification task. A machine learning model may be trained on the above mentioned labelled ground-truth prototypes in library LBR. For example, a deep neural network with one or more hidden layer may be used, with the last layer, a softmax-layer, to provide the material type classification. The layer may be exclusive fully connected or may be fully convolutional. Alternatively, the network may include both, fully connected layers and convolutional layers. Instead of neural networks, other machine learning models may be used such as decision trees, random forests or support vector machines SVM, and other ML model configurable for classification tasks.

Turning now again to the statistical module SM, its operation based on the mixture models $GMM_i$ envisaged for the present clustering are now described in more detail. In embodiments it is assumed that the points on each spectral diagram Sj are described as a weighted mixture of n Gaussians (GMM). The density of partial model $GMM_i$ for patch $K_i$/spectral diagram $S_i$ may be written as:

$$f(x, y) = \sum_{i=0}^{n} p_i * N_i(x, y) \quad (2)$$

The $p_i$ are the weights and the number "n" will be referred to herein as the "number of components", or "component number". The N, are different Gaussians with different mean and/or co-variance. The Gaussians are bi-variate for dual imaging as considered herein, but may be multi-variate for spectral imaging based on more than two energy windows. "(x,y)" is a point in the local spectral diagram Sj.

The probability of the pixel (x, y) having been generated by Gaussian $G_i$ is computed as:

$$P((x, y) \in G_i) = p_i * N_i(x, y) / \sum_{i=0}^{n} p_i * N_i(x, y) \quad (3)$$

The Probability of the pixel (x, y) to belong to material $M_j$ may be computed as:

$$P((x, y) \in M_j) = \frac{\sum_{N_j} p_j * N_j(x, y)}{\sum_{i=0}^{n} p_i * N_i(x, y)} \quad (4a)$$

wherein $N_j$ is the set of all Gaussians attributed to material $M_j$.

The probability distribution fitting algorithm as implemented by the statistical module SM is now described in more detail. The fitting algorithm may operate on densities of the probability distribution. The densities may be continuous or discrete. The set of the parameters defining the statistical model is optimized by improving, eg maximizing, the Likelihood or, which is mathematically equivalent, the Log-Likelihood function. The Log-Likelihood function is defined as following:

$$L = \log p(X) = \Sigma(x,y) \log \Sigma_i p_i * N_i(x,y,\mu_i,\Sigma_i) \quad (4b)$$

In embodiments, a Maximum-Likelihood (ML) type algorithm, such as an Expectation-Maximization (EM)-type algorithm may be used. The EM algorithm was described by A Dempster et al in "Maximum likelihood from incomplete data via the EM algorithm", J. Roy. Stat. Soc. Ser. B 39, pp 1-38 (1977). The EM algorithm may be used for data that is generated in modes or through hidden states that generate observables. For present purposes, the different materials in the sample are the hidden states and the spectral diagrams Si are the observables.

In order to compute the set of parameters of the partial model $GMM_i$, which maximizes the likelihood of the model for the given spectral diagram $S_i$, an iterative process in two-steps is used, called the "Expectation" and "Maximization" step respectively. Instead of operating on the likelihood function as such, the log-likelihood function L may be used instead. Multiple iteration cycles may be run until the algorithm converges—within an agreed error margin or other stopping condition—to a maximum of the Log-likelihood function. The maximum may be a local maximum or, less likely, a global maximum.

As such, since the convergence is local, parameters computed in the standard EM setup depend on the initialization of the parameters. Also, in the standard EM algorithm, the higher the component number, the higher the values that the log-likelihood function can obtain. In the standard EM-algorithm, the component number is fixed and assumed known. In practical modelling, the component number should be restricted. Different model selection metrics may be used for this purpose.

In embodiments envisaged herein the model builder MB computes the Bayesian information criterion (BIC) as:

$$BIC = \ln(n) * k - 2 \ln(L) \quad (5)$$

Alternatively, the Akaike information criterion (AIC) is used:

$$AIC = 2 * k - 2 \ln(L) \quad (6)$$

wherein:—
k is the number of parameters of the model $GMM_i$:
n is the number of data points in the spectral diagram for which the model is built
L is the maximized value of the Likelihood/log-Likelihood of the model.

For each model GMMi for a respective patch/spectral diagram Si, a set of M Gaussians are initialized and optimized by applying the Expectation-Maximization (EM). This may be repeated in different EM-runs, for each of a number of different values for M. Specifically, for small patches $K_i$ with diameter up to about 20 pixels, the optimal value for component number is any one of M=1,2,3,4. To compute the optimal model, one computes initial models GMMi with M {1, 2, 3, 4} by running the EM algorithm for each value of n. The final model GMMi is the one whose Likelihood/log-Likelihood function L returns the maximal value for a selection metric, such as BIC or AIC to determine the optimal model for this patch $K_i$. BIC metric has performed well for present purpose. For each patch $K_i$/spectral diagram $S_i$, plural EM algorithms are run for different M's to arrive at the respective partial model GMMi. In general, best component number M's will depend on the patch $K_i$.

In order to facilitate good convergence rates of each model and convergence to a good quality local maximum, it may be beneficial to select the initial centers (means) of the Gaussians at points in the spectral diagram where the density of the values are maximal or are at least higher than a threshold. Alternatively, one may place the Gaussians at points as per the means of the prototype Gaussians in the reference library LBR, if the type of materials for the decomposition are already known, as will be the case for most medical examinations/tasks. The initial covariance matrices of the Gaussians may be initialized arbitrarily or at random, since their correct values are computed in the first iterations of the EM algorithm.

By iterating the Expectation-Maximization steps, the log-likelihood L of the respective model $GMM_i$ is increasing and converges to, in general, a local maximum.

In the expectation ("E")-step, the expectation relative to marginal densities is computed, with hidden states averaged out by summation. Probabilities of all data points (x, y) under the model $GMM_i$ with the current values of parameters to belong to Gaussian k is evaluated:

$$P_k(x,y) = \frac{p_k * N_k\left(x, y, \mu_k, \sum_k\right)}{\sum_{i=0}^{n} p_i * N_i\left(x, y, \mu_i, \sum_i\right)} \quad (7)$$

In the maximization (M)-step, the current parameter set for all Gaussian are updated as per:—

$$m_{k+1} = \sum (x, y) P_k(x, y) \quad (8)$$

$$p_{k+1} = \frac{m_k}{m} \quad (9)$$

$$\mu_{k+1} = \frac{1}{m_k} \sum_{(x,y)} P_k(x, y) * (x, y) \quad (10)$$

$$\sum_{k+1} = \frac{1}{m_k} \sum_{(x,y)} P_k(x, y) * (x, y - \mu_k)^T * (x, y - \mu_k) \quad (11)$$

In (9), "m" indicates the total number of pixels.

A motivation for the proposed local, patch-based probability distribution fitting in spectral domain, as opposed to a global fitting may be understood as follows. Many of spatially restricted fragments of the original images $I_{E1}, I_{E2}$ will represent in general one, two, or at the most three different material types. In these cases, building a partial model GMMi for a given diagram patch $S_i$ in the spectral domain will give a good statistic model, that is one with high likelihoods, which will allow good definition of probabilities for the participating materials on this patch. In particular, by using a family of overlapping patches one can obtain good enough statistics to robustly estimate material-type probabilities for all pixels of the image. The fitting operation attempts to distribute the probability mass, based on the given data in the spectral diagram. Globally, the presence of a given material may be minute, so that its contribution may be "drowned out" when attempting to fit the probability mass globally. By working locally, even small contributions can be duly accounted for. In any one sufficiently small patch, there are likely fewer materials to be found, so there is more probability mass available, and less risk for drowning out of low concentration materials.

The per-patch approach allows "fine-grained" information handling by combiners Σ, Σ'. Contributions from patches which result in models with low likelihood can be ignored in this process. Alternatively, a smooth transition from "good" fully used patches to the "bad" ignored patches can be done by using weighted averaging of the corresponding probabilities. The weighs are a function of the partial model likelihood. The global probability maps computed herein may thus be called "Ensemble Averaging Probability Maps" (EAPM).

Operation of the partial model combiner Σ' is now described first in more detail. After the partial model GMM$_i$ has been optimized, the partial probability of a pixel (x, y) to belong to material M$_j$ may be estimated by partial model combiner Σ:

$$P((x, y) \in M_j) = \frac{\sum_{N_j} p_j * N_j(x, y)}{\sum_{i=0}^{n} p_i * N_i(x, y)}, \quad (12)$$

wherein N$_j$ is the set of all Gaussians attributed to material M$_j$. Eq (11) thus allows computing partial material probability map which may be sufficient for local examination.

Operation of the global combiner Σ is now described in more detail. Global combiner Σ allows combing the partial models by ensemble averaging into a global probability map.

The partial probabilities contribute to the global probabilities maps per material. We assume that for each pixel of the original image there is a plurality of local values of probabilities. We can ensure this by building the family of the kernels with center at every pixel and some non-zero radius. This approach may generate a large amount of data and hence robustness, but may increase computation time. In order to strike a decent balance, one may use a sparse family of overlapping kernels, where the distance between two centers is for example about a ⅓ of the kernel radius. Herein, sparsity relates to the amount of overlap. The sparser the less overlap there is.

In one embodiment, global combiner Σ assembles the partial probabilities into the global map by averaging per pixel. For each pixel i=(x,y) of the image, its probability to represent material M, is defined as the average of some or all probabilities defined by all partial models GMM$_i$, whose kernel/patch K$_{xy}$ contains this pixel:

$$P((x, y) \in M_j) = \frac{\sum_{K_{xy}} p_j(x, y)}{N(K_{xy})} \quad (13)$$

where N(K$_{xy}$) is the number of all kernels/patches, containing this pixel (x, y). The p$_j$'s are probabilities computed in different partial models relevant to the given pixel (x,y). Whilst for the partial maps eq (11) only the partial model for a single patch is used, in the global map eq (13) all models for patches that cover a given pixel are taken into account and averaged over, but models with likelihood may be dropped or down-weighted as will be explained in the following.

Since the mixture models envisaged herein are statistical models strongly dependent on data distribution, the quality of the models for different patches may differ widely, especially because the component number has been restricted on practical grounds. For the most of the smaller patches, up to four Gaussians will provide a reasonable Likelihood of the model, although for some patches likelihood may still deteriorate to very low values. For better results in computing the global probability map, it is proposed to apply one or two thresholds to exclude partial results with low Likelihood when combing the global probability map. With this policy, only contributions from patches with "good" statistics are used, whilst patches with "bad" statistics are ignored. This policy helps to achieve greater robustness.

For the single threshold embodiments, eq (13) above may be used. Only results from those patches, for which the partial model p$_j$ yields likelihood greater than a threshold TH, are admitted into the summation of the denominator, with p$_j$>TH.

Rather than a hard thresholding, a weighted averaging of the partial probabilities may be used in alternative embodiments, where the weight is a function of the likelihood of the partial model:

$$P((x, y) \in M_j) = \frac{\sum_{k_{xy}} C(L(k_{xy})) p_j(x, y)}{\sum_{k_{xy}} C(L(k_{xy}))} \quad (14)$$

The definition of the weight function requires two thresholds T$^L$, T$^H$, and a transition function from zero to one. For example, a sinusoidal curve over interval (−π, π) may be used, scaled appropriately. For example, the weight function may be defined as:

$$C(L(k_{xy})) = \begin{cases} 0, \text{ if Likelihood} < LowThreshold \\ 1, \text{ if Likelihood} > HighThreshold \\ 0.5 + 0.5 * \left( \operatorname{Sin}\left( \frac{L - T^L}{T^H - T^L} - 0.5 \right) * PI \right) \text{otherwise} \end{cases} \quad (15)$$

Alternatively, the soft-max-function or tanh—may be used, or others still.

Figure 4:
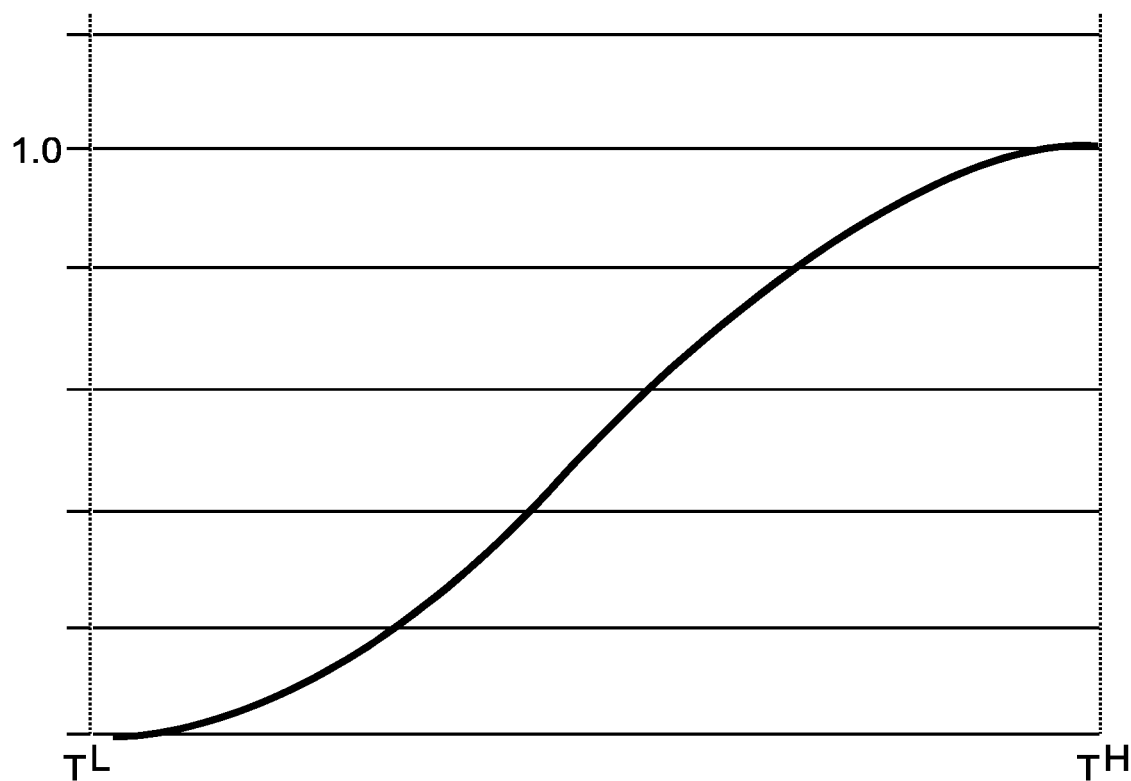
FIG. 4 shows a soft-thresholding curve as may be used in the material decomposition system.

FIG. 4 shows an illustration of such a smoothed threshold weight function which may be used in embodiments by the classifier CL. T$^L$, T$^H$ indicate the low and high thresholds, respectively.

Figure 5:
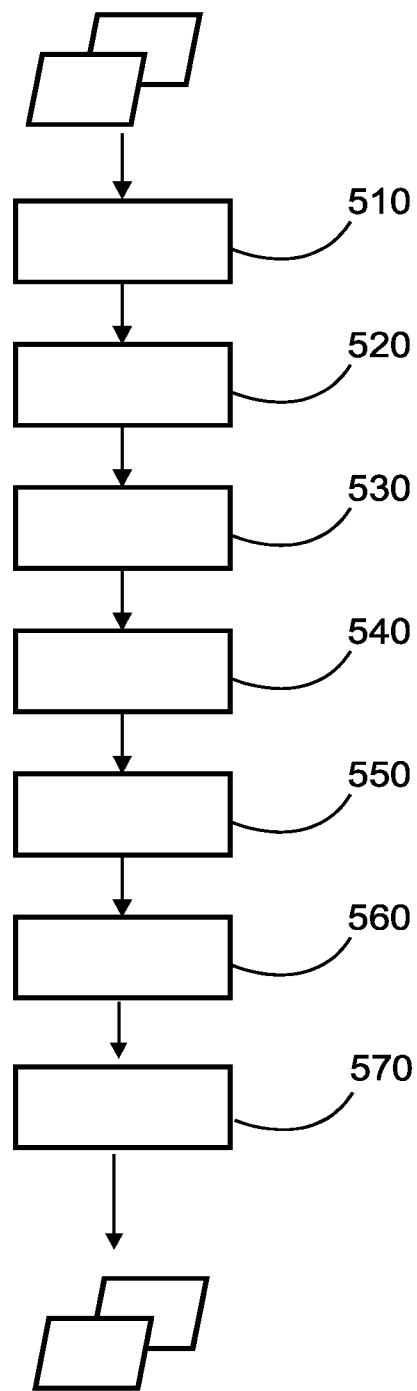
FIG. 5 shows a flow chart of a method of spectral image-based material decomposition.

Reference is now made to the flow chart in FIG. 5 which illustrates steps of the proposed spectral-image based material decomposition method. It will be understood that the method is not necessarily tied to the architectures described above and may be understood as a teaching in its own right.

At step S510, spectral imagery is received. This may include two or more energy images. In the above described detector- or source-enabled spectral imaging modalities the energy images are natively spatially registered. In some other cases, though less preferable, a registration algorithm may be used first to spatially align the energy images.

At step S520 patches, that is sub-sets, in the spectral imagery are defined.

At step S530 for each patch in the spectral imagery, a spectral diagram is computed. Steps 520 and 530 may be reversed in order, in which case the spectral diagram is computed first for the whole spectral imagery, and the patches are defined then.

At step S540 a plurality of probability distributions are fitted per spectral diagram or patch. A mixture model such as a Gaussian mixture model may be used where each of the plural probabilities distributions are fitted in combination. A linear combination may be used. Other models may be used instead. The fitting operation results in partial models GMM$_i$ for each patch.

At an optional step S550, the fitted probability distributions in some or each partial model $GMM_i$ are classified according to material type. A library of pre-stored prototypes may be used for the classification. Machine learning may be used for classification instead.

In step S560, the partial models per image location are combined into partial probability maps, one for each image location. Combination may be done by averaging. Partial models for those patches are combined that cover that image location.

At optional step S570 the partial probability maps are averaged to obtain a global probability map for the whole image plane. The combination may include averaging, in particular ensemble averaging. The averaging may include weighted averaging of the partial models.

In embodiments, in step S570, low likelihood partial models are down-weighted relative to others with higher likelihood to so implement a soft-thresholding. A hard thresholding may be used instead, where partial models with likelihoods below a threshold are ignored entirely and are not included in the combination to form the global map.

The proposed patch-based fitting approach in spectral domain allows securing the following advantages: The local maxima may no longer depend strongly on different initializations. Even materials represented by a small number of pixels that may attract very low weights in a global model can be adequately accounted for in partial models per patch (see below the discussion of FIG. 8).

In a conventional global model fitted at once, the original position and covariance of the different Gaussians can change significantly during the optimization process, so that initial attribution of material-type may be not justifiable. But this attribution can be safely done in the proposed localized per-patch approach Gaussians obtained in a standard optimization may sometimes extend over large areas with significant overlap with other Gaussians, thus making a classification difficult, if not impossible. With per-patch fitting in spectral domain as proposed herein, such extension and overlap can be curbed. The per-patch approach allows avoiding the likelihood to grow to inflated values. If one were to apply the EM optimization to the whole image, then even the model selection metrics BIC or AIC would not help to meaningfully curb the likelihoods.

Again, whilst the above has been explained with main reference to Gaussians and Gaussian mixture models, this is not limiting and all the above is of equal application to other mixture models not necessarily involving Gaussians. Also, statistical cluster schemes other than mixture models may be used instead, such as factor analysis. Also, the groups of probability distributions $\{P^j\}$ of a partial model may be related other than in a linear combination as assumed in standard mixture models. More involved relationships may be 10) used instead. Furthermore, instead of using the EM-algorithm or any of its cognates, Monte-Carlo-Markov Chain methods, moment matching, spectral methods (eg, based on singular value decomposition) or graphical methods may be used instead to fit the group of probability distributions $\{P^j\}$ per patch.

Figure 6:
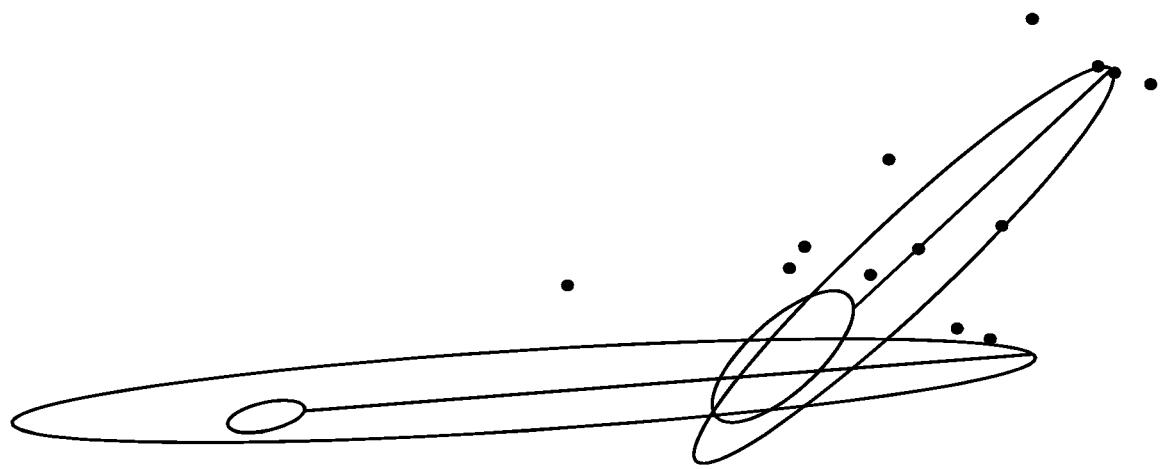
FIG. 6 shows a spectral diagram clustered based on fitted probability distributions.

FIG. 6 is an illustration of a spectral diagram for the whole image, not merely for a patch. The point clouds represents points in the spectral diagram with the ellipses (four are shown) representing the clustering. Each ellipse represents a two times o-level line of a respective Gaussian. The example model contains 4 Gaussians. Each Gaussian may be labelled as one of four materials: Air, Bone, Iodine and Kidney Stone, for example. In the global probability map, the probability of a pixel to belong to one of those materials is estimated from the fitted mixture model. Pixels on the spectral diagram may be visually encoded, for example by color-coding or grey value. The color codes for the material with highest probability. The global or partial probability maps as computed herein may be visualized on the spectral diagram (as in FIG. 6) for the whole plane of the spectral imagery, or on a patch. Alternatively, the probability map may be visualized accordingly in spatial domain, optional displayed together with the original spectral imagery, such as with one of the energy images or with a combination thereof. For example, the probability map may be superimposed as an overlay on the spectral imagery in spatial domain, with suitable color- or grey-value coding.

Figure 7:
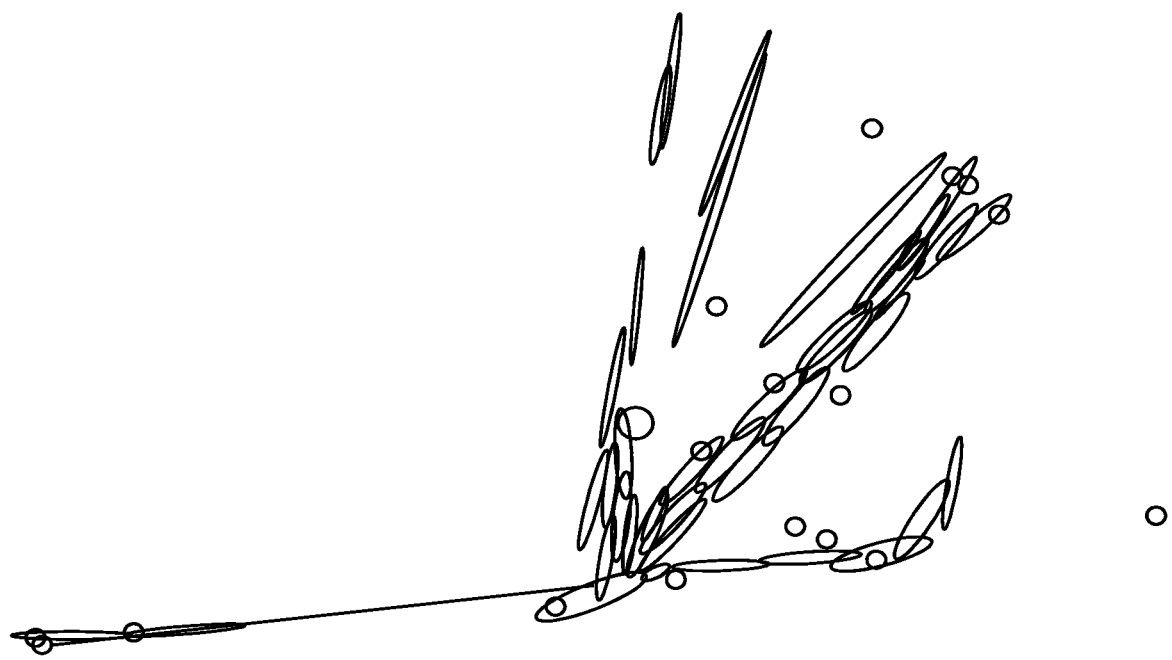
FIG. 7 shows a library of probability distributions pre-classified according to material type.

FIG. 7 is an illustration of a library LBR of prototype probability distributions as may be used for classification purposes as described above. Each ellipse represents a respective material type, although for each material more than one ellipse can be present in the library. The representation in FIG. 7 is in spectral domain as in FIG. 6.

Figure 8:
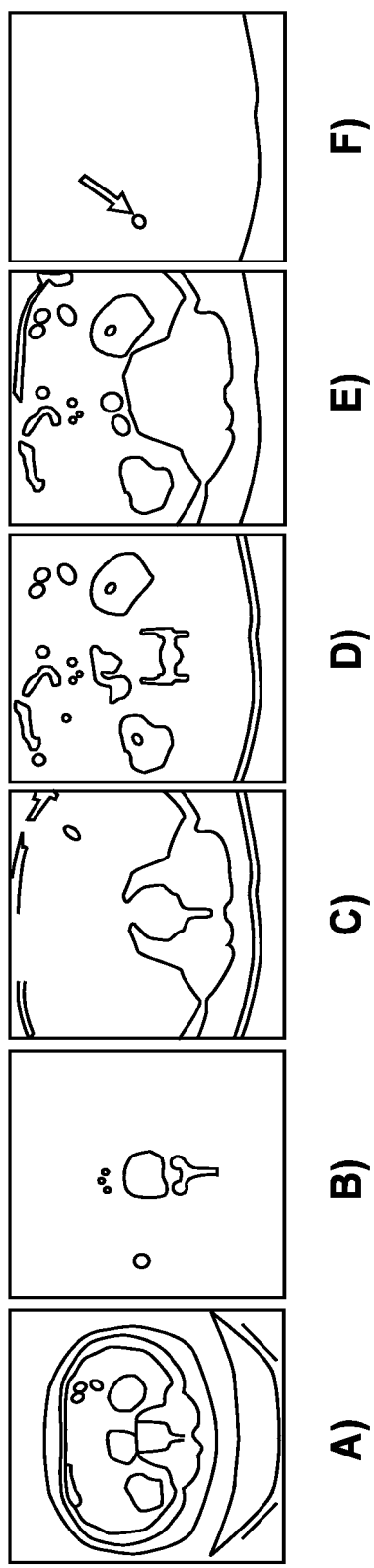
FIG. 8 shows schematic exemplary representations of probability maps obtainable by the material decomposition method or system.

FIG. 8 is an illustration of the ability of the proposed material decompositioner MD to detect even minute amounts of a material in a more than four-material type decomposition. FIG. 8 illustrates a 5-material decomposition for abdominal imagery with pane A) indicating the original spectral imagery such as the high or low image or a combination thereof. Pane B) represents a probability map for bone. Pane C) represents a probability map for soft tissue, and pane D) a probability map for Iodine. Pane E) is a probability map for fat. Notably, pane F) shows a probability map for uric acid. As can be seen, the proposed method and system MD can detect even small amounts of a material, such as in this case uric acid, indicated by the small arrow in pane F).

The proposed material decompositioner MD allows better utilizing spectral data for medical applications where automatic segmentation or material decomposition is required. The probability maps as computed herein can be used in different medical applications, such as in Liver-Fat Quantification, for obtaining virtual unenhanced images, for characterizing renal lesions, for assessing severity of liver fibrosis, to name but a few of such applications. Applications outside the medical fields are also envisaged.

Some or all of the above mentioned design/hyper-parameters may be learned by machine learning. In particular, the size and overlap percentage of the patches, the parameters of the weighting function for averaging may be determined by machine learning from a training data set.

One or more features described herein can be configured or implemented as or with circuitry encoded within a computer-readable medium, and/or combinations thereof. Circuitry may include discrete and/or integrated circuitry, a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A computer system for spectral material decomposition, comprising:
   a memory that stores a plurality of instructions; and
   a processor that couples to the memory and is configured to execute the plurality of instructions to:
      fit, per patch in input spectral imagery, a set of probability distributions to a respective vector spectral diagram for the respective patch, the patch being one of a plurality of patches in the input spectral imagery, the input spectral imagery obtained by operation of a spectral imaging apparatus, the spectral imagery including at least two energy images, and
      combine the probability distributions into a probability map indicative of material type probabilities per image location in the input spectral imagery.

2. The system of claim 1, wherein the processor is configured to perform a combination operation to combine, per image location in the input spectral imagery, the set of probability distributions fitted to spectral diagrams for the one or more patches that include the respective image location, to obtain the probability map.

3. The system of claim 1, wherein the combination operation includes adapting contributions of the probability distributions to the probability map based on their likelihood values per image location.

4. The system claim 1, wherein the combination operation includes averaging the probability distributions per image location.

5. The system claim 1, wherein the processor is configured to classify the probability distributions according to material type.

6. The system of claim 5, wherein the number of different material types is at least four.

7. The system of claim 1, wherein the processor is configured to fit the probability distributions based on a maximum likelihood algorithm.

8. The system of claim 7, wherein the maximum likelihood algorithm includes the expectation-maximization algorithm.

9. The system of claim 1, wherein the number of probability distributions per spectral diagram is based on a model selection metric.

10. The system of claim 1, wherein the set of probability distributions represents a mixture model.

11. The system of claim 1, wherein the set of probability distributions comprise Gaussian distributions.

12. A computer-implemented method of spectral material decomposition, comprising:
   fitting, per patch in input spectral imagery, a set of probability distributions to a respective vector spectral diagram for the respective patch, the patch being one of a plurality of patches in the input spectral imagery, the input spectral imagery obtained by operation of a spectral imaging apparatus, the spectral imagery including at least two energy images; and
   combining the probability distributions into a probability map indicative of material type probabilities per image location in the input spectral imagery.

13. The method of claim 12, further comprising combining, per image location in the input spectral imagery, the set of probability distributions fitted to spectral diagrams for the one or more patches that include the respective image location, to obtain the probability map.

14. The method of claim 12, further comprising adapting contributions of the probability distributions to the probability map based on their likelihood values per image location.

15. The method of claim 12, further comprising averaging the probability distributions per image location.

16. The method of claim 12, further comprising classifying the probability distributions according to material type.

17. The method of claim 12, wherein the probability distributions are fitted based on a maximum likelihood algorithm.

18. The method of claim 17, wherein the maximum likelihood algorithm includes the expectation-maximization algorithm.

19. The method of claim 12, wherein the number of probability distributions per spectral diagram is based on a model selection metric.

* * * * *